United States Patent [19]

Desbois

[11] Patent Number: 4,788,346

[45] Date of Patent: Nov. 29, 1988

[54] PROCESS FOR THE PREPARATION OF PARA-NITROPHENOL

[75] Inventor: Michel Desbois, Rillieux La Pape, France

[73] Assignee: Rhone-Poulenc Chimie, Courbevoie Cedex, France

[21] Appl. No.: 54,852

[22] Filed: May 27, 1987

[30] Foreign Application Priority Data

May 29, 1986 [FR] France .................................. 86 07918

[51] Int. Cl.[4] ....................... C07C 79/24; C07C 76/02
[52] U.S. Cl. .................................................... 568/706
[58] Field of Search ......................................... 568/706

[56] References Cited

U.S. PATENT DOCUMENTS 3,911,031 10/1975 Hoch et al. ......................... 568/706
3,917,719 11/1975 Baldwin et al. ..................... 568/706

*Primary Examiner*—Werren B. Lone
*Attorney, Agent, or Firm*—Finnegan, Henderson, Farabow, Garrett and Dunner

[57] ABSTRACT

A process for the preparation of para-nitrophenol by bringing a phenyl ester of an inorganic acid into contact with a nitrating agent in the presence of liquid hydrofluoric acid and a hydrolysis of the nitrated product obtained is carried out either simultaneously or in sequence with the nitration.

12 Claims, No Drawings

PROCESS FOR THE PREPARATION OF PARA-NITROPHENOL

The present invention relates to a process for the preparation of para-nitrophenol. More particularly, it relates to a process for the nitration of para-nitrophenol from phenyl esters of inorganic acids.

The direct nitration of phenol is industrially unprofitable because it produces a mixture of ortho- and para-isomers in which the ortho-isomer is predominant and difficult to separate from the para-isomer. Various processes have been proposed to avoid this disadvantage, especially processes starting with diphenyl carbonate, which is nitrated and then hydrolyzed to give para-nitrophenol.

German Patent No. 2,557,614 discloses a process for the direct nitration of diphenyl carbonate wherein the concentration of nitric acid initially introduced into the reaction medium is less than 85% and the concentration of nitric acid introduced later is greater than 95%. The yields of bis(4-nitrophenyl) carbonate never exceed 78% because the ratio of para- to orthto-isomers is not optimal and the para-isomer never exceeds 80%.

French Patent No. 76/33,148 also discloses the nitration of diphenyl carbonate in concentrated sulfuric acid. This process provides yields of bis(4-nitrophenyl) carbonate of approximately 80%, the ratio of para- to ortho- substituted derivatives being higher than in the process of the German patent.

However, processes which employ sulfuric acid as the solvent have several disadvantages. Sulfuric acid is a strong oxidizing agent and has a high viscosity, which causes stirring problems. Moreover, the high boiling point of sulfuric acid prevents easy recycling and leads to the difficulty of disposing of the sulfate effluents.

The present invention makes it possible to avoid the use of sulfuric acid and its related problems. It provides a process for the preparation of para-nitrophenol comprising the steps of nitrating a phenyl ester of an inorganic acid with a nitrating agent in the presence of liquid hydrofluoric acid and hydrolyzing the nitrated product obtained by the nitration reaction, the hydrolysis either being carried out simultaneously with the nitration reaction or being carried out sequentially with the nitration reaction.

The phenyl esters of inorganic acids employed within the scope of the present invention are preferably selected from the group consisting of phenyl borates, phenyl phosphates, phenyl sulfates, phenyl carbonates, phenyl arsenates, phenyl atimonates, phenyl orthosilicates and monophenyl selenates.

It is preferred to use diphenyl carbonate or triphenyl phosphate.

The nitrating agent may be selected from the group consisting of commonly available nitric acids such as fuming nitric acid or 65% nitric acid; alkali metal salts of nitric acid such as, in particular, sodium or potassium nitrates; and nitronium salts such as nitronium tetrafluoroborate. The use of commercially available nitric acids with a concentration greater than 65% is greatly preferred.

The hydrofluoric acid employed as solvent is preferably anhydrous although the presence of water does not cause additional reaction problems since some water is already present from the nitric acid.

Where the reaction is carried out starting with very labile raw materials such as triphenyl phosphate, inert solvents in addition to hydrofluoric acid may be used. Among the solvents which can be used are methylene chloride, carbon tetrachloride, 1,1,2-trifluoro-1,2,2-trichloroethane and 1,1,1-trichloroethane. However, it is preferable to operate in the absence of any solvent other than hydrofluoric acid.

It is preferred to operate with a molar ratio of nitric acid to the number of equivalents of phenyl radicals in the ester ranging from the stoichiometric ratio, 1:1, to 1.5:1 and preferably ranging from 1:1 to 1.2:1.

The molar ratio of hydrofluoric acid to the phenyl ester may be varied within wide limits. However, industrially, it is preferable to maintain the molar ratio at a range from 5:1 to 50:1 and more preferably, at a range from either 5:1 to 20:1 or 10:1 to 50:1.

Since hydrofluoric acid has a low boiling point, it can be recovered easily by distillation and can be recycled into a new batch, leaving a reaction product which is solvent-free.

The reaction temperature preferably ranges from −20° to 150° C. However, when diphenyl carbonate is used as the raw material, it is preferable to have a reaction temperature ranging from 20° to 100° C. and when triphenyl phosphate is used, to have a reaction temperature preferably ranging from 0° to 50° C.

The reaction pressure may vary within wide limits; however, when the reaction temperature is greater than 20° C., the reaction is preferably carried out at a pressure greater than atmospheric to maintain the hydrofluoric acid in a liquid state.

The hydrolysis of the nitrophenyl ester of the inorganic acid, i.e., the nitrated product obtained by the nitration reaction, is carried out either at the same time, i.e, simultaneously, as the nitration or in sequence with the nitration reaction. For example, when triphenyl phosphate is used, and the reaction temperature ranges from 0° to 50° C., the hydrolysis of the nitrated ester is carried out, at least in part, concomitantly with the nitration reaction. On the other hand, when diphenyl carbonate is used and the reaction temperature ranges from 20° to 100° C., the dinitrodiphenyl carbonate can easily be isolated since it is stable, and hydrolysis may then be carried out sequentially in a manner known to one skilled in the art. Alternatively, hydrolysis can be carried out directly in the reaction mixture by heating.

When the reaction is complete, the hydrofluoric acid may be removed by distillation and the crude reaction mixture may then be recovered. The desired nitrophenyl ester is then extracted from the crude mixture with a solvent such as methylene chloride.

Para-nitrophenol is used as an intermediate or synthesis in the pharmaceutical industry.

The present invention will be described more completely using the following examples, which should not be regarded as limiting the invention. Compositions are in weight percent unless otherwise indicated.

EXAMPLE 1

NITRATION OF PHENYL CARBONATE 100 g (5 moles) of ahydrous hydrofluoric acid, 21.4 g (0.1 mole) of diphenyl carbonate and 14.5 g (0.22 mole) of 98% nitric acid were introduced in sequence into a 250 ml stainless steel reactor stirred with a bar magnet. The reactor was closed and the contents were then heated and maintained at a temperature of 50° C. for 3 hours 45 minutes, while stirring. After cooling to approximately 0° C., the reactor was opened and the crude reaction mixture was poured onto 200 g of crushed ice. The heterogeneous mixture obtained was extracted with 2×100 cm³ of methylene chloride. The organic phases were combined, washed with 2×100³ of water and dried. After evaporation, 26.7 g of a compound essentially consisting of nitrophenyl carbonate (as determined by infrared spectroscopy) were collected. After hydrolysis in an alkaline medium and analysis by liquid chromatography, a p-nitrophenol:o-nitrophenol isomer ratio of approximately 85:15 was observed.

EXAMPLE 2

NITRATION OF PHENYL PHOSPHATE

The reaction was carried out in a manner similar to that in Example 1 (procedure and treatments), with the following compounds and conditions:

| | |
|---|---|
| HF | 100 g (5 moles) |
| triphenyl phosphate | 32.6 g (0.1 mole) |
| 98% HNO₃ | 24 g (0.36 mole) |
| duration | 2 hours 50 minutes |

42 g of a mixture consisting of the following (determined by high performance liquid chromatography) were collected:

| | |
|---|---|
| triphenyl phosphate | 0% |
| nitrophenyl phosphate | 0% |
| benzoquinone | 0.2% |
| phenol | 6.9% |
| p-nitrophenol | 24.4% |
| o-nitrophenol | 11.8% |
| m-nitrophenol | 0.1% |
| 2,4-dinitrophenol | 50.5% |
| unknowns | 6.1% |

EXAMPLE 3

NITRATION OF PHENYL PHOSPHATE DISSOLVED IN CH₂Cl₂

The reaction was carried out in a manner similar to that in Example 1 (procedure), with the following compounds and conditions (methylene chloride is introduced first):

| | |
|---|---|
| CH₂Cl₂ | 200 cm³ |
| HF | 20 g (1 mole) |
| triphenyl phosphate | 15 g (0.046 mole) |
| 98% HNO₃ | 9.5 g (0.15 mole) |
| temperature | approximately 10° C. |
| duration | approximately 1 hour |

When the reaction was complete, an aliquot part (30 cm³) of the lower phase which settled (chestnut-brown colored solution) was treated with 10 g of NaF and filtered. Analysis by high performance liquid chromatography gave the following results:

| | |
|---|---|
| triphenyl phosphate | 5.9% |
| nitrophenyl phosphate | 55.2% |
| p-nitrophenol | 25.9% |
| miscellaneous | 13.0% |

The remaining part of the reaction mixture (the upper phase and the remainder of the lower phase) was treated in a manner similar to that in Example 2. 17.5 g of a compound consisting of the following (as determined by high performance liquid chromatography) was thereby obtained:

| | |
|---|---|
| unknowns | 13.6% |
| p-nitrophenol | 70.5% |
| o-nitrophenol | 11.0% |
| triphenyl phosphate | 3.0% |

What is claimed is:

1. A process for the preparation of para-nitrophenol comprising the steps of nitrating a phenyl ester of an inorganic acid with a nitrating agent selected from nitric acids with a minimum concentration of 65%, alkali metal salts of nitric acid and nitronium salts, in the presence of liquid hydrofluoric acid at a temperature ranging from −20° C. to 150° C., and hydrolyzing the nitrated product obtained by said nitration reaction, said hydrolysis being carried out simultaneously with said nitration reaction or said hydrolysis being carried out sequentially with said nitration reaction.

2. The process of claim 1, wherein said hydrolysis is carried out simultaneously with said nitration reaction.

3. The process of claim 1, wherein said hydrolysis is carried out sequentially with said nitration reaction.

4. The process of claim 1, wherein the phenyl ester of inorganic acid is selected from the group consisting of phenyl carbonates and phenyl phosphates.

5. The process of claim 4, wherein the phenyl ester of inorganic acid is a triphenyl phosphate.

6. The process of claim 4, wherein the phenyl ester of inorganic acid is a diphenyl carbonate.

7. The process of claim 1, wherein the hydrofluoric acid is anhydrous.

8. The process of claim 1, wherein the molar ratio of the nitrating agent to the number of equivalents of phenyl radicals in the ester ranges from 1:1 to 1.5:1.

9. The process of claim 9, wherein the molar ratio of the nitrating agent to the number of equivalents of phenyl radicals in the ester ranges from 1:1 to 1.2:1.

10. The process of claim 1, wherein the molar ratio of liquid hydrofluoric acid to the phenyl ester ranges from 5:1 to 50:1.

11. The process of claim 5, wherein the temperature at which the reagents are brought into contact ranges from 0° C. to 50° C.

12. The process of claim 6, wherein the temperature at which the reagents are brought into contact ranges from 20° C. to 100° C.

* * * * *